United States Patent [19]

Jasin et al.

[11] Patent Number: 4,713,337

[45] Date of Patent: Dec. 15, 1987

[54] METHOD FOR DELETION OF A GENE FROM A BACTERIA

[75] Inventors: Maria Jasin, Ft. Lauderdale, Fla.; Paul R. Schimmel, Lexington, Mass.

[73] Assignee: Massachusetts Institute of Technology, Cambridge, Mass.

[21] Appl. No.: 688,612

[22] Filed: Jan. 3, 1985

[51] Int. Cl.[4] .............................................. C12N 15/00
[52] U.S. Cl. .............................. 435/172.3; 435/172.1; 935/11
[58] Field of Search .......................... 435/172.1, 172.3; 935/9

[56] References Cited

PUBLICATIONS

Kleckner et al., J. Mol. Biol., 116:125-159, 1977.
Scherer et al., PNAS (USA), 76(10):4951-4955, 1979.
Jasin et al., J. Bacteriol., 159(2):783-786, 1984.
Clark, Ann. Rev. Genet., 7:67-86, 1974.
Miller, J., in *Experiments in Molecular Genetics*, Cold Spring Harbor, pp. 196-200, 1972.
"Replacement and Amplification of Bacterial Genes with Sequences Altered in Vitro" by N. I. Gutterson et al., *Proc. Natl. Acad. Sci., vol. 80, pp. 4894-4898 (1983)*.
"Use of Cloned mtl Genes of *Escherichia coli* to Introduce mtl Deletion Mutations into the Chromosome" by C. A. Lee et al., *J. Bact.*, vol. 153, pp. 685-692 (1983).
"[12] One-Step Gene Disruption in Yeast" by R. J. Rothstein, *Methods in Enzymology*, vol. 101, pp. 202-211, (1983).

*Primary Examiner*—Thomas G. Wiseman
*Assistant Examiner*—Thomas D. Mays
*Attorney, Agent, or Firm*—Patrea L. Pabst

[57] ABSTRACT

Disclosed is a method for the deletion of a gene from a bacteria using a single step procedure that is applicable to any essential or nonessential gene which has been cloned. The process requires the construction of chromosomal deletions by transformation of a cell strain with linear DNA fragments containing a locus for resistance to an antibiotic, or any other gene allowing for rapid phenotypic selection, flanked by sequences homologous to a closely spaced region on the cell chromosome. By selecting for a double-crossover event between the homologous sequences, shown by the antibiotic resistant or other detectable phenotype, a chromosome disruption can be selected for which has effectively deleted an entire gene.

If the gene is essential to viability, the bacteria may be transformed with a plasmid which has a temperature-sensitive replicon and a wild-type allele of the essential gene. When *E. coli* is used as the host strain, it is preferable to use a cell strain which carries the recBC and sbcB mutant alleles which inactivate exonucleases which degrade linear DNA fragments. The sbcB mutation supresses the Rec− phenotype of recBC cells so that homologous recombination functions via an alternative pathway. This plasmid maintains cell viability when the chromosomal copy of the desired gene has been deleted, but the resulting cells have a temperature-sensitive phenotype to provide a means for eliminating the plasmid.

A key feature of the present invention utilizing extrachromasomal genetic material to maintain the desired phenotype once a gene has been deleted is that the bacteria have a RecA+ phenotype or its equivalent at the time of transformation with the linear DNA fragments, which is immediately changed to a RecA− phenotype once recombination of the fragments has occurred to prevent recombination of the extrachromosomal genetic material with homologous sequences on the chromosome.

11 Claims, 4 Drawing Figures

METHOD FOR DELETION OF A GENE FROM A BACTERIA

ND OF THE INVENTION

The Government has rights in this invention pursuant to Grant Number NIH-5-R01-GM23562-08 awarded by the National Institutes of Health.

Many applications require the construction of special bacterial strains which have a particular genetic background. These genetic backgrounds are the framework in which specific recombinant DNA plasmid constructions are tested to determine whether they can provide functions which are missing from the background of the bacteria. If such functions are provided by the recombinant plasmid, then there is positive evidence that a particular genetic locus or loci is encoded by the plasmid. The construction of genetic backgrounds is therefore a vital step in the subsequent cloning and investigation of specific genes.

The most common backgrounds are those in which a single mulation is present in a specific gene on the bacterial chromosome. This may result in synthesis of a defective version of the protein encoded by that gene, resulting in a specific cellular dysfunction. Correction of the cellular dysfunction, by introduction of a specific recombinant plasmid, is suggestive evidence that the relevant gene has been cloned onto the specific plasmid. However, a mutant protein may not be silent and may undergo interactions with other components, thereby creating the appearance that the plasmid gene encodes the entire active protein when it does not. This can seriously confuse the analysis. A much less ambigious approach is one in which the gene in question has been deleted. In these circumstances, there is no production whatsoever of mutant protein.

There are two obstacles which have to be overcome. One is to develope a method which will create a deletion in a defined target within the bacterial chromosome. The second is to generalize the approach so that even essential genes can be deleted. This is because many of the genes of interest are essential ones. The deletion of an essential gene normally would result in cell death.

Essential proteins includes enzymes of glycolysis, enzymes associated with amino acid or sugar biosynthesis, enzymes and factors associated with protein and nucleic acid bissynthesis (including both RNA and DNA), enzymes required for the synthesis of cofactors for oxidation, reduction, methylation and transamination processes, and enzymes necessary for synthesis of essential lipids and polysaccharides or of any other essential molecule, including various nucleic acids, such as transfer or ribosomal RNAs, and segments of nucleic acids, such as gene regulatory elements.

It is therefore an object of the present invention to provide a method wherein an organism is produced which does not contain genetic material coding for the molecule which is to be cloned and expressed in the organism.

A further object of the present invention is to provide a method whereby a deficient organism which is to be used for cloning an essential gene remains viable even under restrictive conditions.

SUMMARY OF THE INVENTION

Disclosed is a method for the deletion of a gene from a bacteria using a single step procedure that is applicable to any gene that has been cloned. The procedure depends upon site-directed recombination of linear DNA fragments with sequences on the chromosome. The method is analogous to a procedure used to give insertions by homologous recombination into specific plasmid genes.

The basic strategy for construction of chromosomal deletions is to transform the bacteria or other cells with linear DNA fragments which contain an antibiotic resistant or other phenotypically detectable gene segment flanked by sequences homologous to a closely spaced region on the cell chromosome. By selection for a double-crossover event within the homologous sequences (the antibiotic resistant phenotype), a chromosome disruption occurs which, if appropriately designed, can effectively delete an entire gene.

A plasmid which has a temperature-sensitive replicon and a wild-type allele of the desired gene is used to restore or maintain the phenotype produced by the deleted gene. This plasmid maintains production of the desired protein, and therefore cell viability if the encoded protein is essential to cell growth, when the chromosomal copy of the desired gene has been deleted. However, since the resulting cells have a temperature-sensitive phototype, the expression of the plasmid gene may be easily prevented by culturing the host strain at an elevated temperature. The resulting deficient host strain may then be used to screen other mutated and cloned genes for their ability to produce the desired protein.

BRIEF DESCRIPTION OF THE DRAWINGS

FIG. 1 (b) shows restriction maps of plasmids pMJ520 and pMJ525 which were used for construction of the chromosomal deletions. These plasmids were constructed as follows. The Kan$^r$ gene was inserted into the HpaI site of alaS of pMJ301 to give pMJ510. The kan$^r$ insertion is a 2.9-kb SmaI fragment from pSE116, described by S.J. Elledge et al., *J. Mol. Biol.*, 164:175–192 (1983) and places the Kan$^r$ gene in the same orientation as alaS. Plasmid pMJ510 was constructed from an EcoRI partial digest of pMJ520, followed by a BamlII complete digest and isolation of the largest EcoRI-RamHI fragment. This vector fragment was ligated to a 1.8 kb BamHI-EcoRI fragment which contains the 5' end of the recA gene described by A. Sancar, *Proc. Natl. Acad. Sci. U.S.A.*, 76:3144–3148 (1979). Plasmid pMJ525 was constructed from a ligation of the larger HindIII SalI fragment of pMJ520 with the HindIII-SalkI Kan$^r$ gene fragment from transposon Tn5 described by S.J. Rothstein, *Cold Spring Harbor Symp. Quant. Biol.*, 45:99–105, (1981). Ori, Origin.

FIG. 2 (B) is a Southern blot analysis according to the method of T. Maniatis et al., described in *Molecular Cloning* (Cold Spring Harbor Laboratory, N.Y., 1982) pp. 382–389, of alaS chromosomal deletions. Chromosomal DNA was isolated and probed with the fragment shown in FIG. 2 (A). The first four lanes show a PatI digest of chromosomal DNA; the last three lanes show a BamHI-SalI digest. Numbers next to the lanes are in kb.

DETAILED DESCRIPTION OF THE INVENTION

Figure 1A:
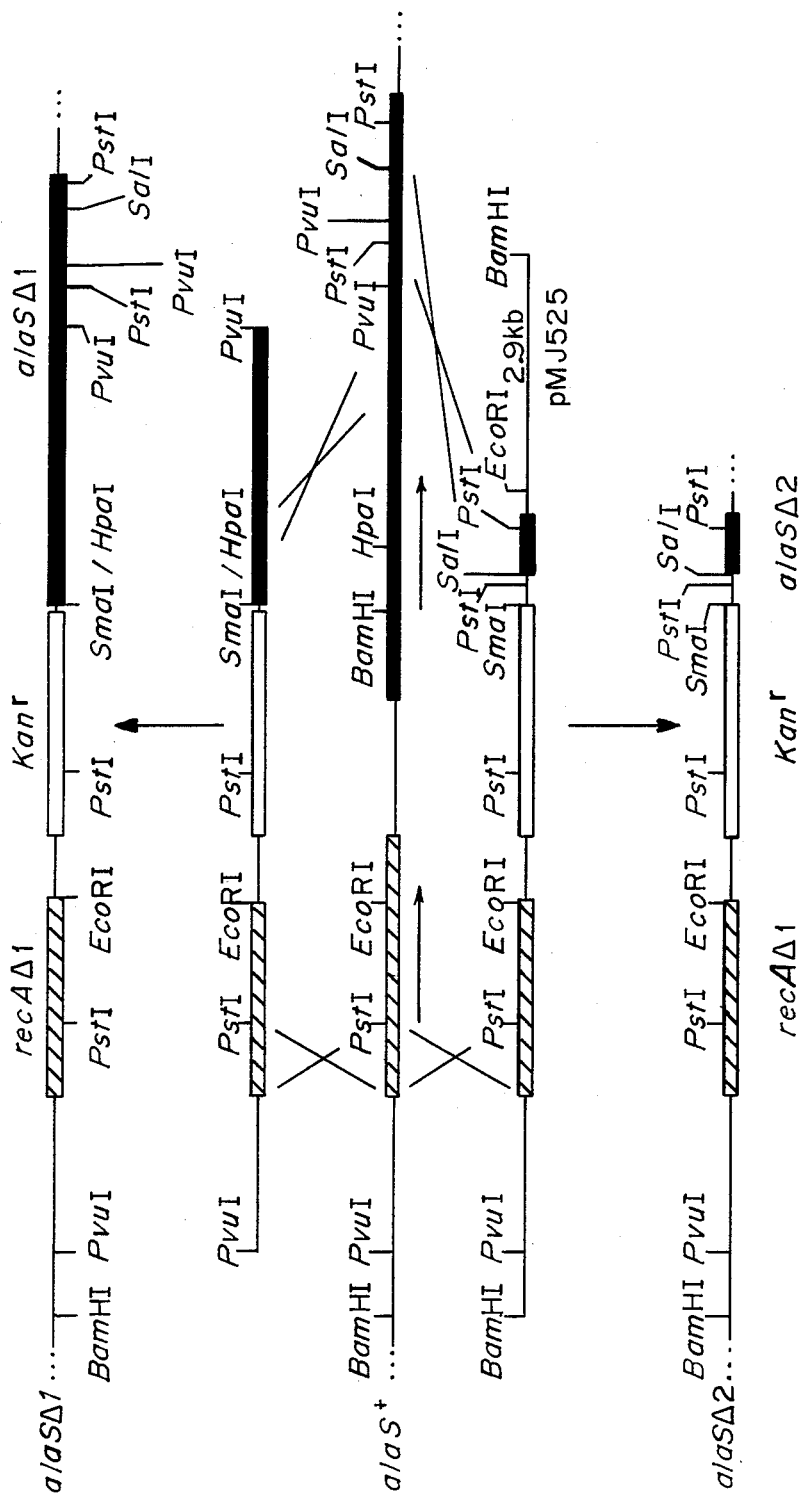
FIG. 1 (a) is a diagram of the construction of chromosomal deletions. The hatched portion of the chromosome refers to the recA gene. The solid portion of the gene refers to the alaS gene. Linear fragments from pMJ520 and pMJ525 were transformed into E. coli JC7623(pMJ901). Selection was for Kan$^r$ clones on LB plates containing 25 micrograms of kanamyein per ml. These were screened for temperature sensitivity (inability to grow at 42° C.) and UV sensitivity (cell death at 20 J/m$^2$), and colonies with this phenotype were presumed to have integrated the transformed fragment via homologous recombination in the manner shown. Strain JC7623 was obtained from G. Walker, and described by S.R. Kushner et al, *Proc. Natl. Acad. Sci. U.S.A.*, 68:824–827 (1971). Plasmid pMJ901 was costructed from a ligation of the 2.9 kb alaS BalI-EcoRI fragment of pMJ301, described by M. Jasin et al., *Cell*, 36:1089–1095 (1984), into the 7.4 kb SmaI-EcoRI vector fragment of pJJS1002 described by J.J. Sninsky et al, *Gene*, 16:275–286 (1981). Plasmid pJJS1002 is an 18 kb derivative of pPM103 which is a temperature-sensitive replication mutant of pSC101, described by P.A. Meacock, *Mol. Gen. Genet.*, 174:135–147 (1979).

The present invention is a method for deleting any gene from a bacterial strain, while maintaining the viability of the bacteria if the gene encodes an essential molecule and deletion of the essential gene results in a lethal phenotype. The gene to be deleted is provided on a plasmid with a temperature sensitive replicon. The cells now have a temperature sensitive phenotype. When the cells are grown at an elevated temperature under conditions which allow rapid detection of the absence of the desired molecule, complementation of this phenotype by introduction of a DNA fragment refused onto a stable plasmid is strong evidence for cloning of the gene which has been deleted from the chromosome.

The method whereby the DNA fragment is introduced involves the construction of linear DNA fragments which have sequences which are homologous to closely spaced regions on the chromosome in the bacteria. These sequences correspond to those which flank each side of the gene of interest. An antibiotic resistant locus such as kan$^r$, which encodes a protein which makes the bacteria resistant to the antibiotic, is placed between these flanking sequences. The linear DNA segment is introduced into a specific cell strain and selection is done for a double, reciprocal recombination which will delete the target gene and insert the antibiotic resistant locus into its place. As a result of the insertion of the antibiotic resistant gene, the cells are now resistant to the antibiotic. Cells which do not contain the insertion are eliminated by growing the bacteria in a medium containing the antibiotic.

Any other gene which allows for rapid screening of the cells containing a double, reciprocal recombination may be used in place of a gene for antibiotic resistance. For example, any gene for an essential protein, including enzymes, cofactors, proteins which are necessary for the synthesis of essential lipids, polysacharides, nucleic acids, and other protein molecules such as receptors, as well as nucleic acids which have functional activity such as ribozymes may be used. Other genes which confer a detectable phenotype on the cell strain such as sensitivity to temperature or ultraviolet radiation, auxotrophism for a sugar, amino acid, protein or nucleotide, or any other phenotype which can be detected by chemical indicators either in vitro or in vivo assay, or an immunoassay for a specific cellular component may also be used. Such chemical, radioactive, or immunological screening assays are well known to those skilled in the art.

In one application, in which the goal is to produce and purify a foreign protein, and the microorganism encodes its own version of the protein, the gene for the microorganism's own protein is eliminated. The gene for the foreign protein is then inserted and the protein produced. The purification process is thereby simplified since there is no contamination by the host protein.

In a second application, a plasmid is used to introduce a gene into an organism which typically contains a mutation in the gene to be investigated which results in a negative phenotype for the product of the gene to be investigated. Failure of the organism to produce a biologically active form of the protein encoded by the mutated gene may confer a lethal phenotype under certain defined conditions. Usually this is at a temperature, designated as the restrictive temperature, at which the mutant protein denatures or otherwise undergoes inactivation. The cloned gene which is introduced is selected for by virtue of its ability to confer cell viability or any other detectable phenotype for the desired protein at the restrictive temperature. The acquisition of viability or other detectable phenotype at the normally restrictive temperature is evidence that the gene of interest has been cloned.

The major problem with this second system is that the defective host protein may interact with a protein produced from the introduced plasmid. This interaction may stabilize the defective host protein enough so that its activity is restored, even at the restrictive temperature. In this case, the restoration of growth at the restrictive temperature would be a false positive, that is, the growth would not be due to activity encoded by the clone DNA segment. This problem holds true for all selections based on complementation of a phenotype which is due to a defect in a specific protein. Such phenotypes include temperature sensitivity, amino acid auxotrophics or any other auxotrophies which result from a lack of synthesis of a key ingredient such as a sugar, nucleotide, critical protein or nucleic acid, or cofactor used for oxidation, reduction, or transamination reactions.

The problem of "false positives" also exists for cloned DNA pieces which are created to encode enzyme fragments as a means to define the catalytic core or to define any segment which achieves a specific purpose, such as a piece which undergoes self-association, binds to a specific ligand or receptor, or forms a specific complex or array with one or more additional components. In these cases, the engineering of protein fragments, which are tested in a host cell that encodes a defective version of the protein of interest, is seriously hampered if the defective host protein interacts in any way with the engineered pieces.

In the present invention, specifically designed linear DNA fragments are used to create a deletion of a gene by cito-specific recombination. These fragments are transformed into host cells such as *E. coli* which have a recBC sbcB phenotype or its equivalent; these two mutations inactivate nucleases which normally degrade linear DNA fragments.

Cell viability or the detectable phenotype is maintained during the procedure by provision of the gene encoding the desired protein on a recombinant plasmid that has a temperature-sensitive replicon, so that the cells which contain the deletion have a temperature sensitive phenotype. To achieve the deletion by recombination with the linear DNA fragments, it is necessary for the cells to have a Rec+ phenotype which is derived from Rec A+, or its equivalent. Once recombination has occurred, the cell must immediately be changed to RecA− or else the temperature sensitive plasmid will recombine with homogolous sequences on the chromosome.

The RecA− phenotype may be achieved by simultaneous inactivation of RecA during the transformation with linear fragments or, after the transformation, by immediately introducing RecA− by mating with an appropriate RecA− strain or by transduction with a phage which carries a RecA− gene segment. Recombination or mutagenesis may also be effective means of making the cell RecA−. The RecA gene is necessary in order for the gene encoding the desired protein to be incorporated into the organism. However, the plasmid will be incorporated unless the RecA gene is immediately removed.

The present invention is further described by the following non-limiting example.

In this example, linear DNA fragments were constructed which contained sequences homologous to those flanking the gene for E. coli alanyl LRNA synthetase. The Kanr locus was inserted between these sequences. Selection was made for acquisition of resistance to the antibiotic, Kanamycin. As few as 240 base pairs are needed to achieve the second crossover. Cell vaibility was maintained by a temperature-sensitive plasmid which encodes alanyl LRNA synthetase. Candidates from this selection were characterized further. Proof of the predicted deletion was accomplished by DNA blot hybridization. With this cell strain it was then possible to test alanyl LRNA synthelase gene fragments to determine whether specific fragments provide the function missing from the chromosome.

The basic strategy for construction of chromosomal deletions is to transform E. coli with linear DNA fragments which contain a Kan$^r$ gene segment flanked by sequences homologous to closely spaced regions on the E. coli chromosome. By selection for a double-crossover event within the homologous sequences (Kan$^r$ phenotype), one can select for a chromosome disruption which, if appropriately designed, effectively deletes an entire gene. Transformations are done into strain JC7623, which carries the rocBC and sbcB mutant alleles. The recBC and sbcB mutations inactivate exonucleases which degrade linear DNA fragments as described by P.J. Goldmark & S. Linn, J. Biol. Chem 247:1849–1860 (1972) and S.R. Kushner et al, Proc. Natl. Acad. Sci. U.S.A. 68:824–827 (1971). Also, the sbcB mutation suppresses the Rec− phenotype of recBC cells, so that homologous recombination functions via an alternative pathway. Because alaS is an essential gene, transformations were done into JC7623(pMJ901). Plasmid pMJ901 has a temperature-sensitive replicon and a wild-type allele of alaS. This plasmid maintains cell viability when the chromosomal copy of alaS has been deleted, but the resulting cells have a temperature-sensitive phenotype.

In a recA+ background or its equivalent, integration of plasmid pMJ901 can occur through homologous recombination at residual alaS sequences on the interrupted chromosome. Because recA is adjacent to alaS on the chromosome, as disclosed by B.J. Bachman, Microbiol. Rev. 44:1–56(1980), it was possible to design linear DNA fragments which, when transformed into E. coli, simultaneously deleted a portion of recA and greater than 90% of alaS. For other genes, a recA allele could be transduced after a gene disruption. Alternatively, the construction can be designed so that there is no homology between the chromosome and the temperature-sensitive plasmid. Loss of recA function may be preferable because some plasmids are more stable in a recBC sbcB recA background, as described by C. L. Basset and S. R. Kushner, J. Bacteriol. 157:661–664 (1984).

Construction of two deletions (ΔalaS1 and ΔalaS2) is shown in FIG. 1a. For both constructions, Kan$^r$ is between a segment encoding an N-terminal fragment of the recA protein and a C-terminal segment of the alaS protein. For each linear DNA fragment, the recA segment and its flanking 5' sequences are about 1.5 kilobase pairs (kb); homologous recombination at these sequences destroys the carboxyl-terminal coding region of recA protein and thereby inactivates it, as shown by A. Sancar et al, in Proc. Natl. Acad. Sci. U.S.A., 76:3144–3148 (1979). The alaS sequences associated with the linear fragment are 1,100 bp (ΔalaS1) and 225 bp (ΔalaS2). The ΔalaS1 deletion effectively removes the amino-terminal one-third of the 2,625 bp alaS coding region. All but the carboxyl-terminal 225 nucleotides are removed in the ΔalaS2 deletion.

Figure 1B:
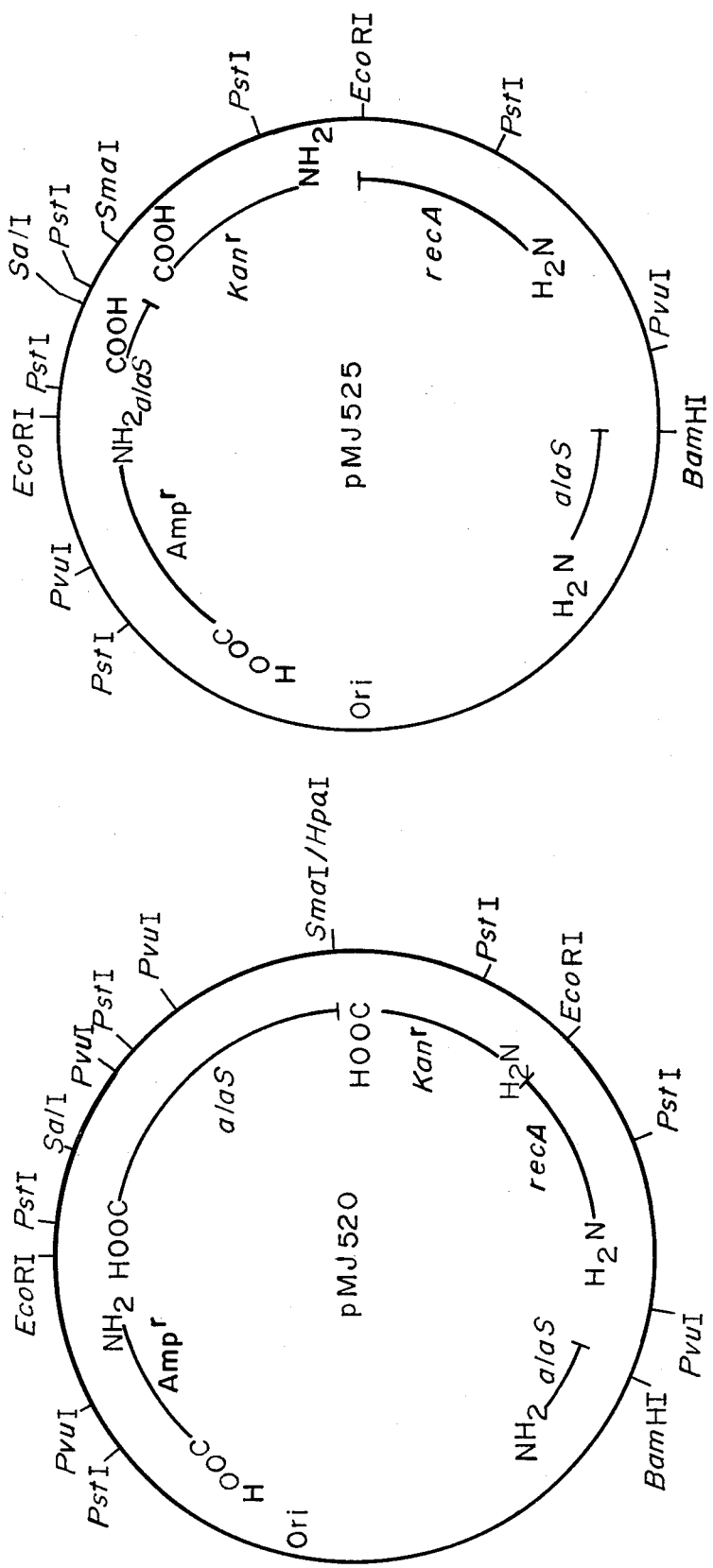

Linear DNA fragments were derived from PvuI-BamHI-cut plasmid pMJ520 (ΔalaS1) and BamHI-cleaved pMJ525 (ΔalaS2) (FIG. 1b). Cells transformed with the linear DNA fragments were first selected for Kan$^r$; these transformants were then screened for the Amp$^s$ and UV- and temperature-sensitive phenotypes. About 30 Kan$^r$ UV$^s$ Amp$^s$ temperature-sensitive transformants were isolated per microgram of PvuI-BamHI-cleaved pMJ520, and about 1 transformant per microgram of BamHI-cut pMJ525 was isolated. Approximately 200 Kan$^r$ Amp$^r$ transformants were obtained per microgram of cut plasmid DNA. Those screened were temperature resistant, presumably because of plasmid recircularization rather than integration.

Figure 2A:
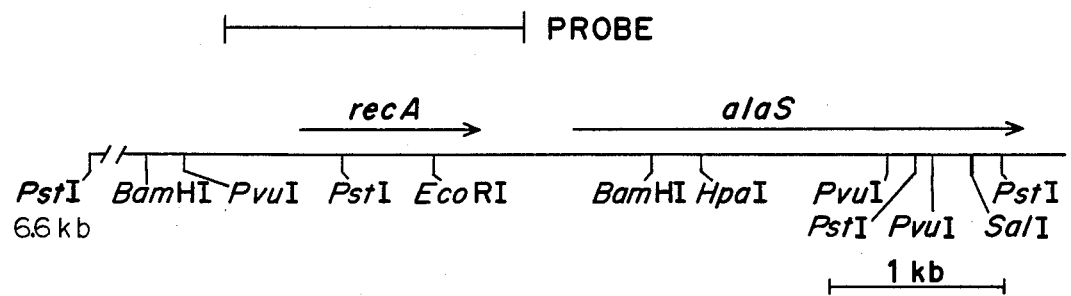
FIG. 2 (A) is a diagram of the derivation of the probe for southern blot analysis. The probe is a 1.8 kb BamHI-EcoRI fragment from the chromosome and contains the 5' end of the recA gene and upstream sequences.

The organization of sequences in strains containing the ΔalaS1 and ΔalaS2 alleles was examined by Southern blot hybridizations. The controls were the parental strains JC7623 and JC7623(pMJ901). A 1.8 kb BamHI-EcoRI hybridization probe was used to differentiate between the various gene arrangements (FIG. 2A). This probe contains a portion of recA and flanking 5' sequences, and is described by A. Sancar et al in Proc. Natl. Acad. Sci. U.S.A., 76:3144–3148 (1979).

Figure 2B:
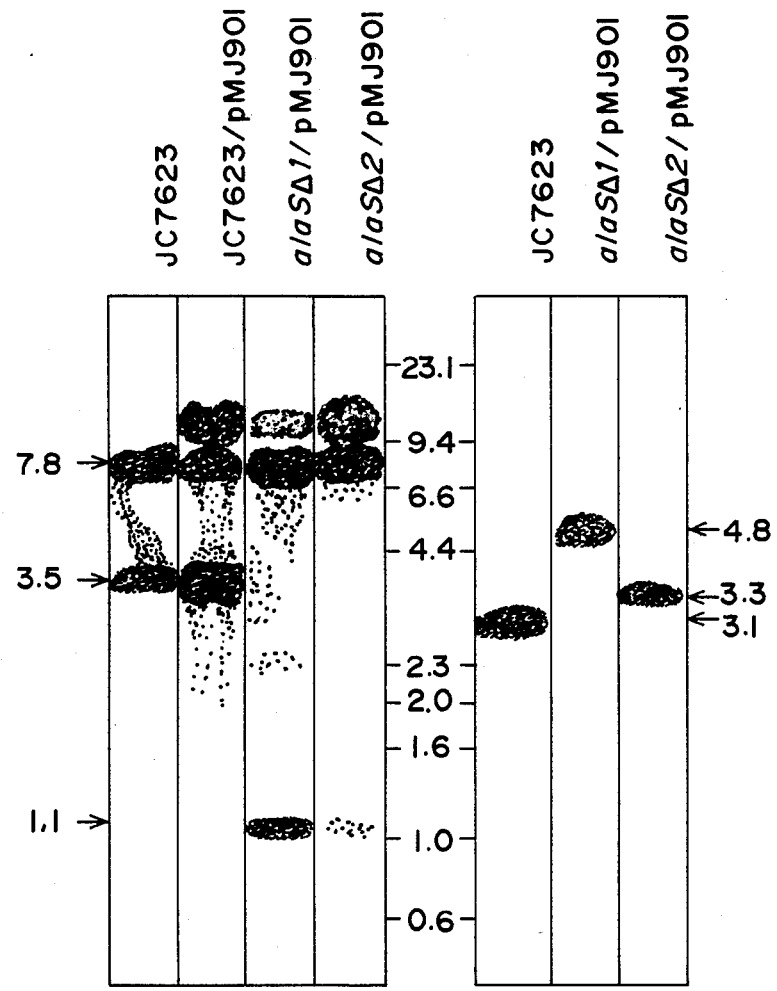

A PstI digest of chromosomal DNA from each of the four strains shows a 7.8 kb band which corresponds to the 5' end of recA, together with several kilobases of upstream sequences; this region is undisturbed in all cases (FIG. 2B). For JC7623 and JC7623(pMJ901), a 3.5 kb fragment also hybridizes to the probe. This corresponds to the PstI fragment which extends from an internal site within recA to a site within the carboxyl-terminal coding portion of alaS (FIG. 2A). For the two deletions, this band is missing and is replaced by a 1.1 kb fragment which extends from the internal PstI site within recA to the downstream PsLI site in the Kanr gene (of. FIG. 1a).

The two deletions wer distinguished by a BamHI-SalI digestion which was examined within the same probe. For JC7623, the expected 3.1-kb BamIII fragment (which encompasses all of the sequences with the probe) is detected. With the deletions, the BamHI site within alaS is lost, and fragments which hybridize to the probe are defined in size by the SaII site within alaS. For ΔalaS1, the resulting BamHI SalI fragment is expected to be 4.8 kb, and for ΔalaS2, which lacks considerably more of alaS, the fragment is expected to be 3.3 kb. The presenc of these fragments is confirmed by the hybridizations (FIG. 2B).

Deletion of the single chromosomal copy of alaS enabled rigorously testing for complementation of gene fragments that encode pieces of alanyl TRNA synthetase. These fragments are discussed in *Nature (London)* 306:441–447 (1983) and *Cell* 36:1089–1095 (1984), the teachings of which are incorporated herein. These were introduced via transformation of a pBR322-derived multicopy plasmid. The mutant allele, alaS5, described by G. Theall et al in *Mol. Gen. Genet.*, 156:221–227 (1977), encodes a polypeptide that gives cells a temperature sensitive phenotype because of a defect in the aminoacylation activity of the mutant polypeptide. This defect can be complemented by specific polypeptide segments which themselves lack catalytic activity. The lack of activity in the pieces is only proved, however, by their failure to complement the ΔalaS2 allele. Complementation of alaS5 by these inactive pieces is due to their physical association with the mutant polypeptide and subsequent reactivation of the alaS5 protein.

The alaS5 allele was cloned into pBR322, and transformed into JC7623 ΔrecA1 KanI ΔalaS2(pMJ901). Cells were plated at 42° C. to induce loss of pM901, and viable transformants were recovered. Amplification of the alaS5 protein by a multicopy plasmid results in sufficient aminoacylation activity to maintain growth at 42° C. This implies that the defective alaS5 protein does not cause extensive and lethal misacylation at the restrictive temperature (42° C.), which could explain the temperature sensitivity of the alaS5 strains.

The approach described in this example for the creation of gene disruptions is useful with any essential or nonessential gene in *E. coli* or other organisms that has been closed. It offers some advantages over other approaches. It is more direct, for example, than methods that, after the disruption, require mating with a strain which has an incompatible plasmid that promotes loss of the nondisrupted reciprocal recombination product. It also has an advantage over the approach in which pBR322-derived plasmid mutants cannot be directly transformed into the disruption strain because it is polA, such as the method described by Gutterson et al in *Proc. Natl. Acad. Sci. U.S.A.* 80:4894–4898 (1983).

In addition to gene disruptions, the method described here can also be used for allele replacements. Any mutation constructed on a plasmid can be transferred with a selectable marker to the chromosome of a recBC sbcB strain to replace the wild-type allele. The only requirement is an efficient screen for integration of the mutation.

We claim:

1. A method for deletion of any gene from an cell with RecA+ phenotype which comprises;
   (a) constructing a linear DNA fragment wherein the fragment has sequences homologous to regions separated by a sequence including nucleotides encoding the gene to be deleted on the cell chremosome, said fragment being of a length and extend of homology as required for binding between the chromosome and said fragment;
   (b) placing a second nucleotide sequence between the homologous sequences in the DNA fragment wherein insertion of the second sequence into the cell chromosome in place of the gene to be deleted and expression of said inserted gene results in a detectable pheno-type;
   (c) introducing the linear DNA fragment into the cell strain;
   (d) selecting for a double reciprocal recombination mediated by the RecA gene by culturing the cells containing the linear DNA under conditions wherein the phenotype encoded by the second nucleotide sequence is detected and cells with a double reciprocal recombination express the detectable phenotype; and
   (e) immediately converting the cells from RecA+ to Reca−.

2. The method of claim 1 wherein the RecA+ phenotype of said cells is converted to RecA− by the inactivation or deletion of the RecA gene upon the introduction into said cells by said linear DNA fragment.

3. The method of claim 1 wherein the RecA gene is deleted or inactivated following a mating of cells of a first strain of *E. coli* with cells of a second strain of *E. coli* wherein cells of second strain are RecA−.

4. The method of claim 1 wherein the cells are converted to RecA− by transduction of RecA+ cells with a phage wherein said phage carriers a RecA− gene segment.

5. The method of claim 1 which further comprises providing extrachromosomal material encoding said deleted gene and introducing said extrachromosomal material into cells of *E. coli* containing said gene deletion after the RecA gene is deleted or inactivated.

6. The method of claim 5 wherein the extra chromosomal material provided is a plasmid.

7. The method of claim 6 wherein the plasmid contains a temperature-sensitive replicon.

8. The method of claim 7 further comprising cultunary the *E. coli* cells at a restrictive temperature to eliminate the plasmid.

9. the method of claim 1 further comprising selecting the gene whose expression results in a detectable phenotype from the group consisting of genes which confer a phenotype on the cell strain of temperature sensitivity, ultraviolet radiation sensitivity, auxotrophism for a sugar, auxotrophism for an amino acid, auxotrophism for a protein, auxotrophism for a nucleotide, and genes which encode for a specific cellular component detectable by chemical, radioactive or immunological screening techniques.

10. The method of claim 1 further comprising selecting *E. coli* cells wherein the genes encoding exonucleases in said cells are deleted or inactivated.

11. The method of claim 1 wherein the *E. coli* cells carries recBC and sbcB mutant alleles which inactivate exonucleases.

* * * * *

UNITED STATES PATENT AND TRADEMARK OFFICE
CERTIFICATE OF CORRECTION

PATENT NO. : 4,713,337
DATED : December 15, 1987
INVENTOR(S) : Maria Jasin et al.

Page 1 of 2

It is certified that error appears in the above-identified patent and that said Letters Patent is hereby corrected as shown below:

```
Column 1, line 5, change "ND" to --BACKGROUND--.
Column 1, line 22, change "mulation" to --mutation--.
Column 1, line 48, change "bissynthesis" to --biosynthesis--.
Column 2, line 26, change "phototype" to --phenotype--.
Column 2, line 62, change "kan^r" to --Kan^r--.
Column 2, line 40, change "kanamyein" to --kanamycin--.
Column 2, line 67, change "Bam 1lI" to --BamHI--.
Column 2, line 68, change "EcoRI-RamHI" to --EcoRI-BamHI--.
Column 3, line 10, change "southern" to --Southern--.
Column 3, line 18, change "Pat I" to --Pst I--.
Column 3, line 54, change "climinated" to --eliminated--.
Column 4, line 1, underline or italicize --in vitro-- and
          --in vivo--.
Column 4, line 42, change "auxotrophics" to --auxotrophies--.
Column 4, line 61, change "cito-specific" to --site-specific--.
Column 5, line 27, change "LRNA" to --tRNA--.
Column 5, line 28, change "Kanr" to --Kan^r--.
Column 5, line 33, change "LRNA" to --tRNA--.
Column 5, line 37, change "LRNA" to --tRNA--.
Column 5, line 49, change "rocBC" to --recBC--.
Column 6, line 63, change "PsLI" to --PstI--.
Column 6, line 63, change "Kanr" to --Kan^r--.
Column 6, line 64, change "(of." to --(cf.--.
Column 6, line 67, change "Bam 1lI" to --BamHI--.
Column 7, line 3, change "SaII" to --SalI--.
Column 7, line 7, change "presenc" to --presence--.
Column 7, line 11, change "TRNA" to --tRNA--.
```

UNITED STATES PATENT AND TRADEMARK OFFICE
CERTIFICATE OF CORRECTION

PATENT NO. : 4,713,337

DATED : December 15, 1987

INVENTOR(S) : Maria Jasin et al.

Page 2 of 2

It is certified that error appears in the above-identified patent and that said Letters Patent is hereby corrected as shown below:

```
Column 7, line 59, claim 1, before "cell" insert --E. coli--.
Column 7, line 59, claim 1, change "cell" to --cells--.
Column 8, line 1, claim 1, change "chremosome" to --chromosome--.
Column 8, line 2, claim 1, change "extend" to --extent--.
Column 8, line 10, claim 1, change "pheno-type" to --phenotype--.
Column 8, line 21, claim 1, change "Reca-" to --RECA-.--.
Column 8, line 47, claim 9, change "the" to --The--.
```

Signed and Sealed this

Twenty-fifth Day of September, 1990

Attest:

HARRY F. MANBECK, JR.

*Attesting Officer*

*Commissioner of Patents and Trademarks*